(12) United States Patent
Oh et al.

(10) Patent No.: US 9,861,674 B2
(45) Date of Patent: Jan. 9, 2018

(54) PHARMACEUTICAL COMPOSITION CONTAINING EXTRACT OF HOUTTUYNIA CORDATA AS ACTIVE INGREDIENT FOR PREVENTING AND TREATING DEMENTIA, PARKINSON'S DISEASE, OR EPILEPSY

(71) Applicant: UNIVERSITY INDUSTRY COOPERATION GROUP OF KYUNG HEE UNIVERSITY, Gyeonggi-do (KR)

(72) Inventors: Myung Sook Oh, Seoul (KR); Hyo Geun Kim, Gyeonggi-do (KR); Hanbyeol Park, Seoul (KR)

(73) Assignee: UNIVERSITY-INDUSTRY COOPERATION GROUP OF KYUNG HEE UNIVERSITY, Gyeonggi-Do (KR)

(*) Notice: Subject to any disclaimer, the term of this patent is extended or adjusted under 35 U.S.C. 154(b) by 735 days.

(21) Appl. No.: 14/249,867

(22) Filed: Apr. 10, 2014

(65) Prior Publication Data

US 2014/0220166 A1    Aug. 7, 2014

Related U.S. Application Data

(63) Continuation of application No. PCT/KR2012/008269, filed on Oct. 11, 2012.

(30) Foreign Application Priority Data

Oct. 12, 2011  (KR) .................. 10-2011-0104179

(51) Int. Cl.
  *A61K 36/78* (2006.01)
  *A61K 36/87* (2006.01)

(52) U.S. Cl.
  CPC ........... *A61K 36/78* (2013.01); *A61K 36/87* (2013.01)

(58) Field of Classification Search
  CPC .............................. A61K 36/78; A61K 36/87
  USPC .................................................. 424/766, 774
  See application file for complete search history.

(56) References Cited

U.S. PATENT DOCUMENTS

| 2002/0006446 A1 | 1/2002 | Chantara et al. | |
| 2011/0020464 A1* | 1/2011 | Ushijima | A61K 35/26 424/580 |
| 2012/0114771 A1* | 5/2012 | Yagi | A61K 36/28 424/764 |

FOREIGN PATENT DOCUMENTS

| CN | 101475553 A | * 7/2009 |
| KR | 1020020015540 A | 2/2002 |
| KR | 1020040094512 A | 11/2004 |

OTHER PUBLICATIONS

Wikipedia.org/wiki/ampelopsin.*
Ampelopsin—Wikipedia free encyclopedia.*
Li, W. et al., "Houttuynia cordada, a novel and selective COX-2 inhibitor with anti-inflammatory activity," Journal of Ethnopharmacology, Jan. 27, 2011, vol. 133, No. 2, pp. 922-927.
International Search Report for PCT/KR2012/008269 dated Mar. 27, 2013, from which the instant application is based, 3 pgs.
Liu, Z et al., "Ampelopsis japonica Makino cools heat and reduces the swelling," Traditional Chinese Veterinary edicine, China Agricultural Press, 4th Edition, Jun. 30, 2011, p. 161, with English translation.
Shi, Li-Juan et al., "Effect of Herba Houttuyniae injection on the ability of learning and memory of mice," J. Southeast Univ (Med Sci Edi), 23(6): 390-393, Nov. 2004, with English Abstract.
Chao, Hong et al., "Serum antioxidase and vitamin E of patients with Alzheimer disease," Chin J Public Health, 2007, vol. 23, No. 12, 1465-1466, with English Abstract.
Lin, Yukun et al., "Oxidative stress and Alzheimer disease," Anat Res, 2009, vol. 31, No. 1, pp. 67-70, with English Abstract.

* cited by examiner

*Primary Examiner* — Chris R Tate
*Assistant Examiner* — Deborah Davis
(74) *Attorney, Agent, or Firm* — Fredrikson & Byron, P.A.

(57) ABSTRACT

Pharmaceutical compositions containing an extract of *Houttuynia cordata* (THUNB) as an active ingredient for preventing and treating dementia, Parkinson's disease, or epilepsy and methods for using the same. Since the extract of *Houttuynia cordata* or the mixture of the extract of *Houttuynia cordata* and the extract of *Ampelopsis japonica* Makino has a cell protection effect and/or a cognition function improved effect in various models including an Amyloid-β induced dementia model, a scopolamine induced dementia model, a 6-hydroxydopamine (6-OHDA) induced Parkinson's disease model, and a Kainic acid induced epilepsy model, the extract of *Houttuynia cordata* or the mixture of the extract of *Houttuynia cordata* and the extract of *Ampelopsis japonica* Makino may be used as the pharmaceutical composition for preventing and treating dementia, Parkinson's disease, or epilepsy and in health foods for preventing and treating dementia, Parkinson's disease, or epilepsy.

14 Claims, 6 Drawing Sheets

[Fig 1]
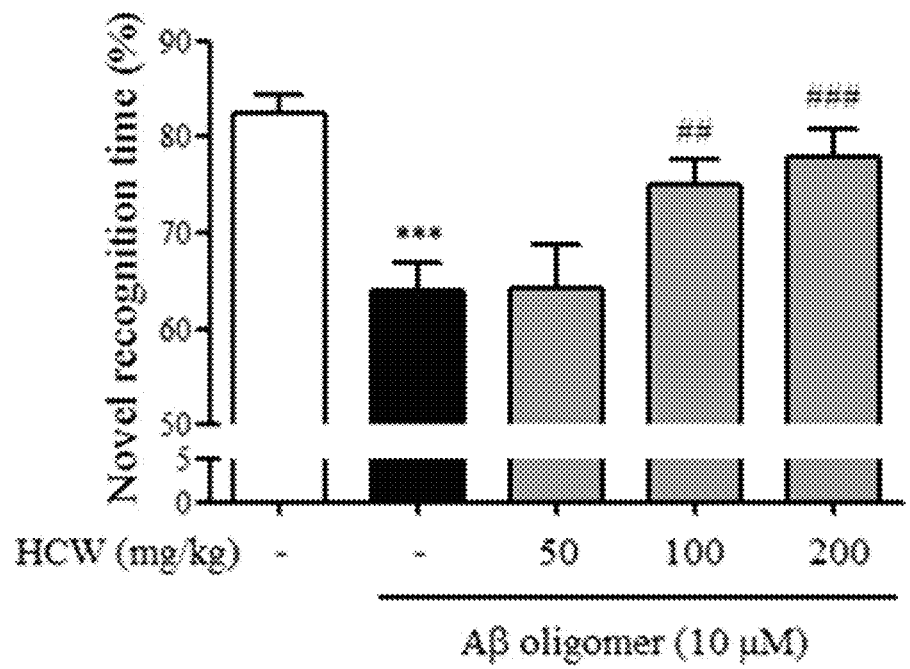
[Fig 2]
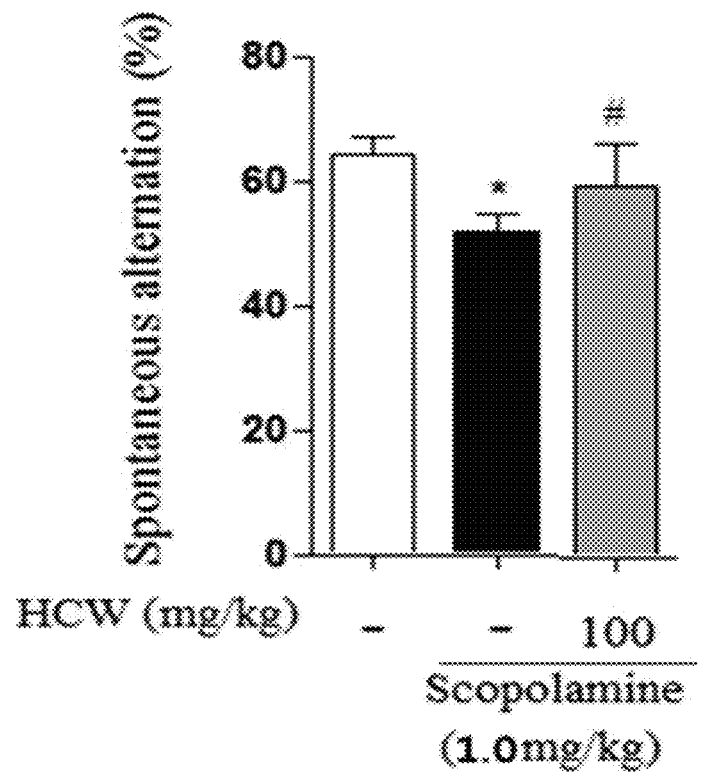

[Fig 3]
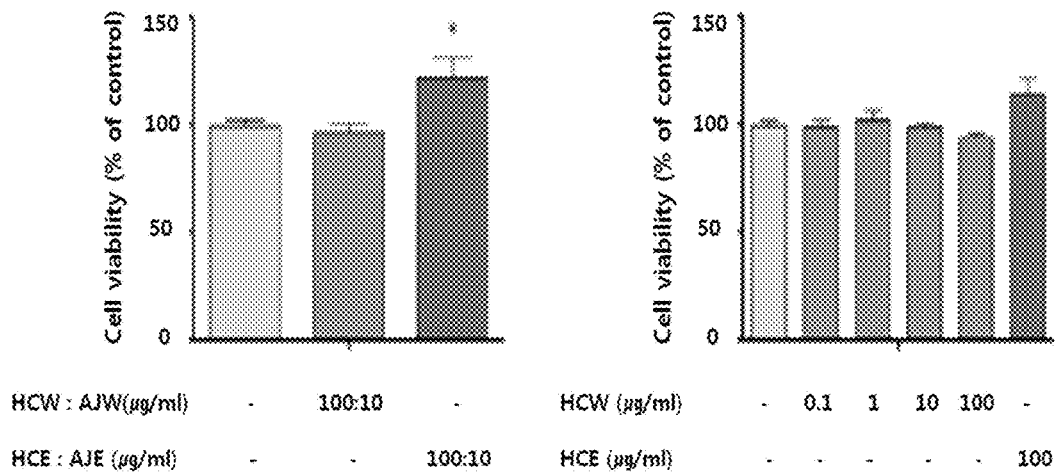
[Fig 4]
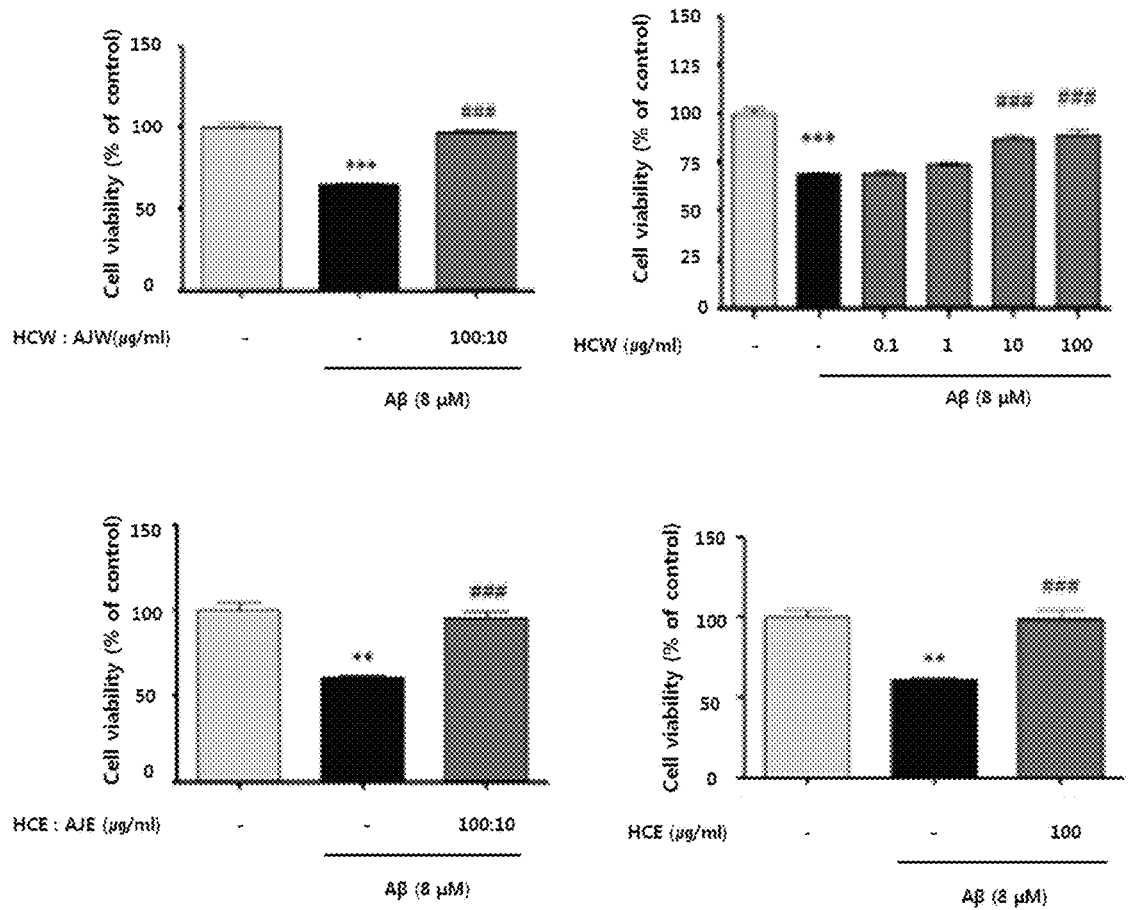

[Fig 5]
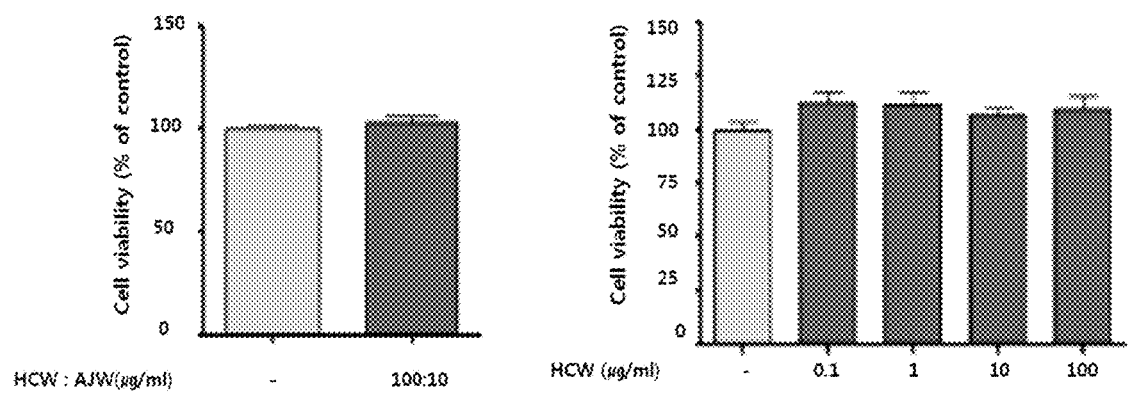
[Fig 6]
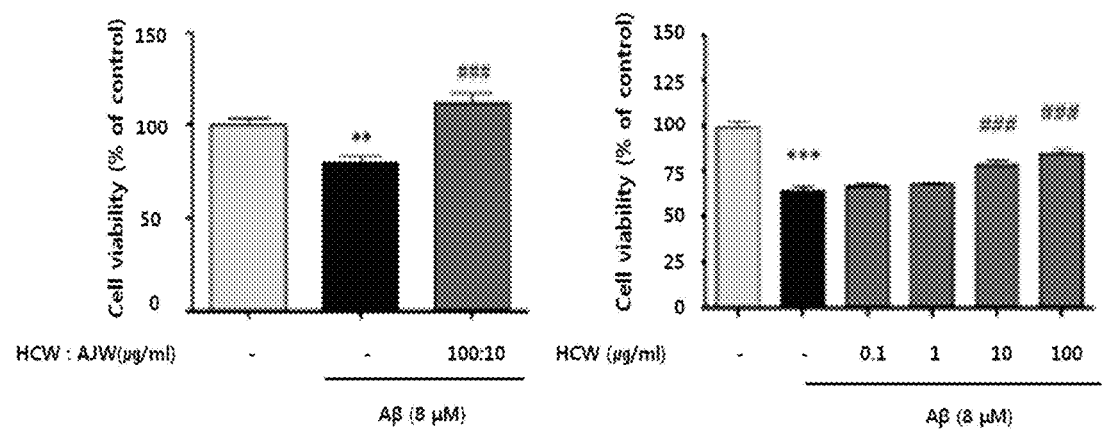

[Fig 7]
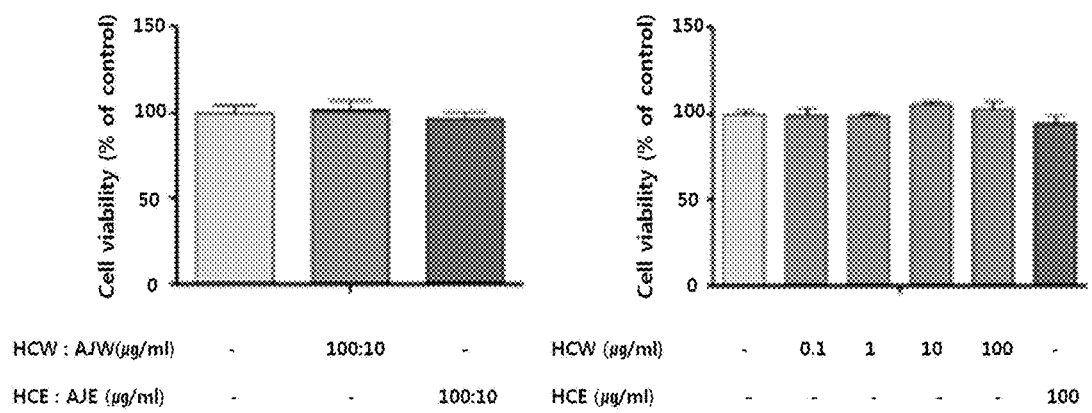
[Fig 8]
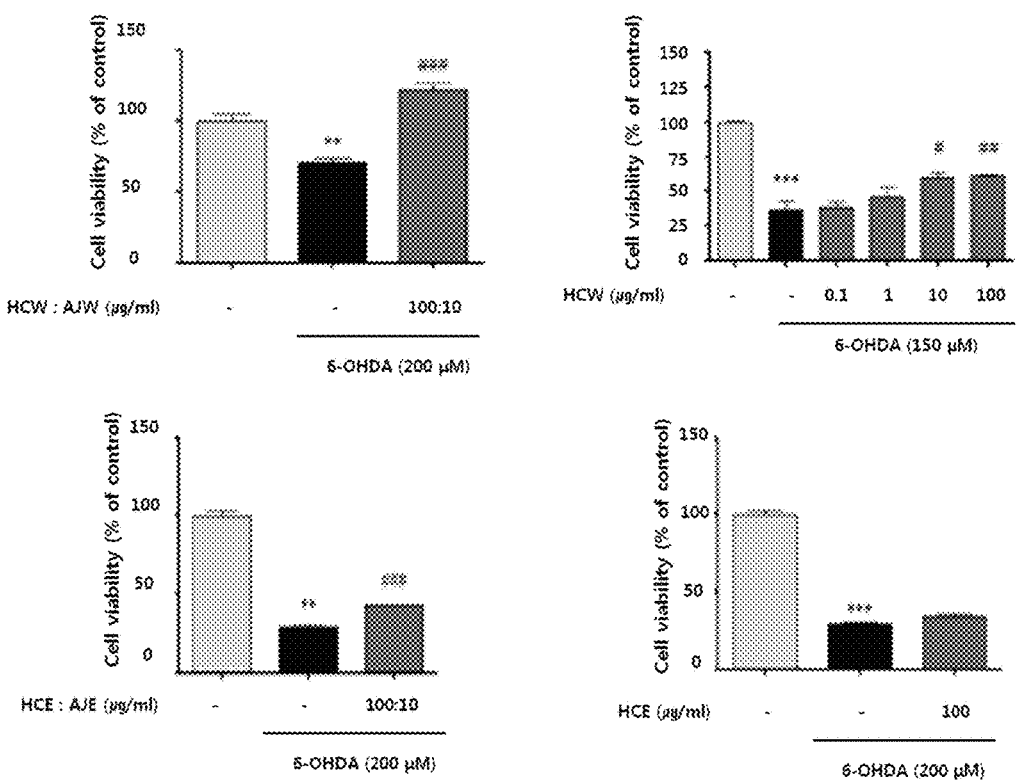

[Fig 9]
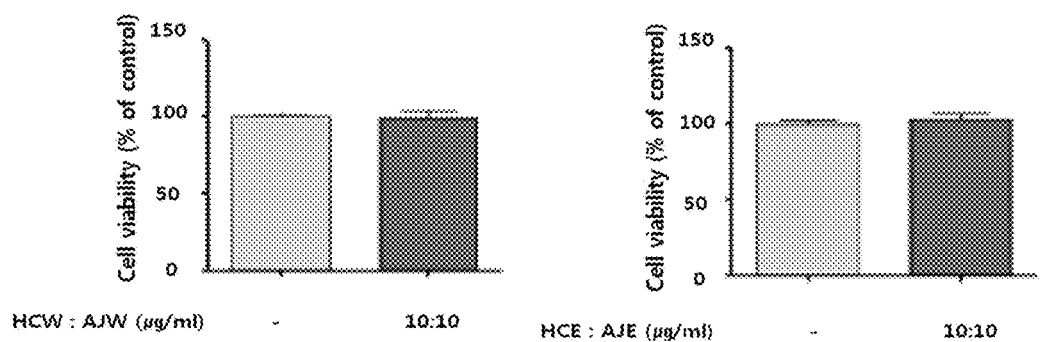
[Fig 10]
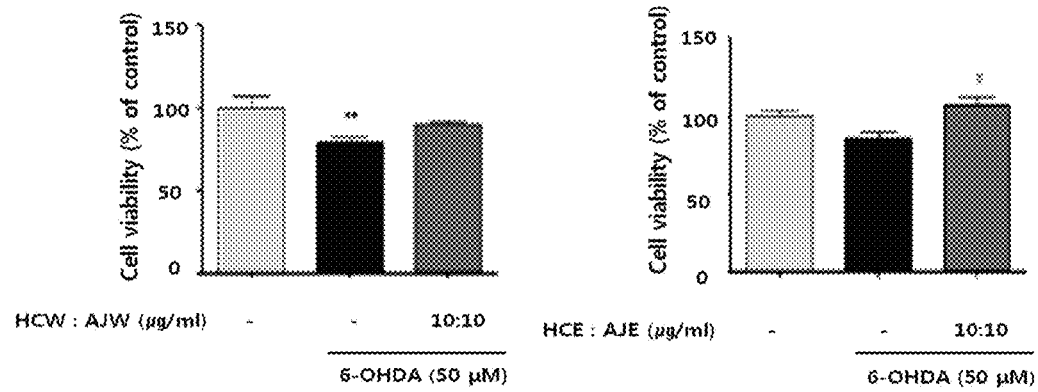

[Fig 11]
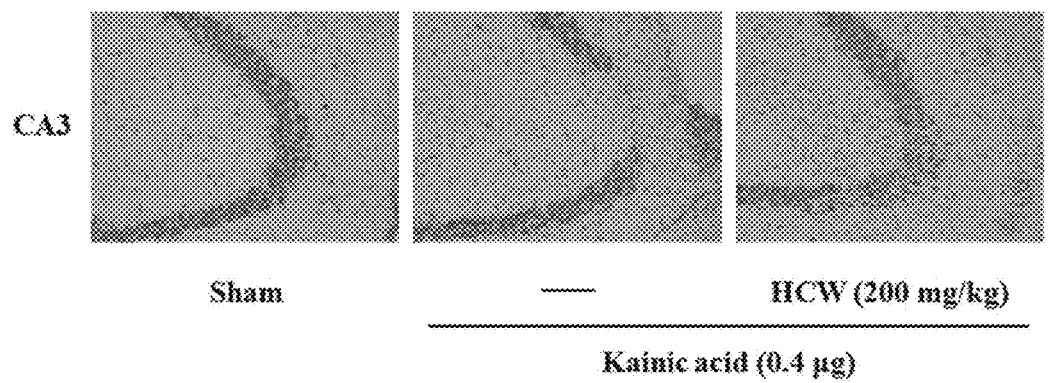
[Fig 12]
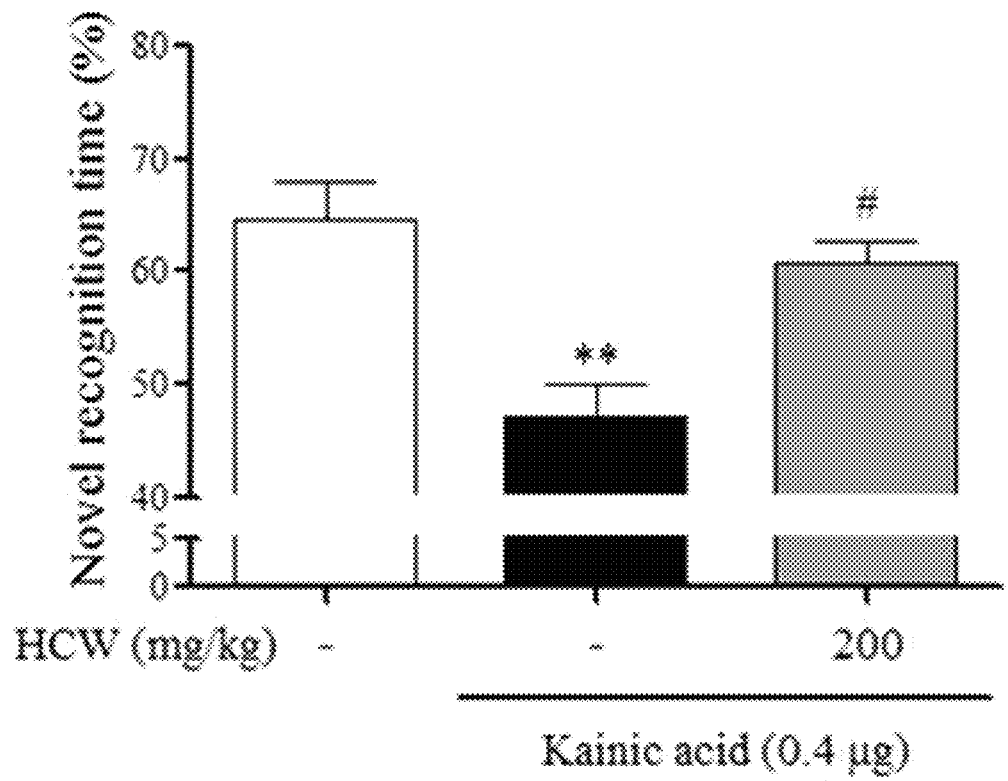

PHARMACEUTICAL COMPOSITION CONTAINING EXTRACT OF HOUTTUYNIA CORDATA AS ACTIVE INGREDIENT FOR PREVENTING AND TREATING DEMENTIA, PARKINSON'S DISEASE, OR EPILEPSY

RELATED APPLICATIONS

This application is a continuation application of International Application No. PCT/KR2012/008269 filed Oct. 11, 2012, and claims priority to Korean Application No. 10-2011-0104179 filed Oct. 12, 2011, the teachings of which are incorporated herein by reference.

TECHNICAL FIELD

The present invention relates to a pharmaceutical composition or a composition for health foods containing preparation plant extracts or a mixture thereof as an active ingredient for preventing and treating dementia, Parkinson's disease, or epilepsy.

BACKGROUND ART

When considering a ratio of the proportion of the elderly people in Korea announced in National Statistics in October 2003, a population of more than 65 years of age in 2000 reached 7.2% of the total population. It is expected that this ratio exceeds 14% to enter into an aging society in 2019. As such, as the aging problem comes to as a social issue, the public interest on characteristics of the aging population and the welfare for the aged such as housing, health, culture, and leisure have been increased, thereby increasing the demand for statistics therefore. The core of this change is that chronic degenerative diseases comes to as a larger problem than all acute infectious diseases which have been the leading cause of the death over the past 50 years due to the increase of the aging population. Particularly, the death due to a cerebrovascular disease among the chronic degenerative diseases has been ranked as the second among death rates due to a single disease.

Dementia has an impairment in normal daily life in profession, social and personal relationships, and means that one or more among four kinds such as a speech impairment, disorientation, poor numeracy, and a change in personality and emotion in addition to a memory impairment. The dementia is a pathological symptom which needs to be distinguished from a normal aging, and classified into Alzheimer's dementia, vascular dementia, and other dementias caused by alcohol addiction, trauma, and a sequela of Parkinson's disease depending on a cause. The vascular dementia causes cerebral infarction, stroke, or the like, and it has been known that brain cells around a disease portion are damaged to cause symptoms in early such as memory loss. On the other hand, the Alzheimer's dementia is a degenerative brain disease caused by the destruction of brain cells, and has symptoms such as memory loss, a change in personality, and poor thinking and slowly progresses, but it has been known that most patients die due to pneumonia and the like within 8 to 10 years. According to recent epidemiological studies, it is reported that risk factors of a cerebrovascular disease such as high blood pressure, diabetes, hyperlipidemia, and heart diseases, cerebrovascular disease increases the incidence of not only vascular dementia but also Alzheimer's dementia, but the cause of a disease or a treating method is still unknown.

As a representative animal test model used for the dementia studies, a dementia mode of a white mouse induced by scopolamine acts as an antagonist to a muscarinic receptor to hinder coupling of acetylcholine and the receptor, and as a result, causes memory and cognitive impairments due to the reduction of a transfer amount of acetylcholine.

The Alzheimer's disease (AD) is characterized by loss of neurons, and a extracellular senile plaque consisting of amyloid β protein (amyloid-beta; Aβ) which is a 39-43 amino acid peptide derived from amyloid precursor protein as a major component. As the results of in vitro and in vivo studies, it is reported that the Aβ or a fragment of the Aβ peptide has a toxicity effect, and as a result, it is shown that the Aβ plays an important role in the incidence of the AD (Butterfield et al., Free Radical Biology and Medicine, 2002, 32:1050-1060; Butterfield et al., Free Radical Biology and Medicine, 2007, 43:658-677). During culture, the Aβ directly induces the death of the neurons, and makes the neurons to be vulnerable to excited toxicity and oxidative damage. An N-methyl-D-aspartate (NMDA) receptor acts as a medium of a selective substrate of Aβ coupling or Aβ-induced glutamate excited toxicity. The NMDA receptor is particularly a ligand-gate/voltage-sensitive cation channel which is highly permeable to Ca2+. A wide increase of $[Ca2+]_i$ directly leads to cell dysfunction, hysteria, or death. Accordingly, as verified by the report that a neurotoxic effect of the Aβ is reduced by (5R,10S)-(+)-5-methyl-10,11-dihydro-5H-dibenzo(a,d)cyclohepten-5,10-imine maleate (MK-801) which is an antagonist of a non-competitive NMDA receptor, Ca2+ flow through the NMDA receptor by Aβ exposure plays a crucial role in the Aβ-induced neurotoxicity. It is believed that formation of reactive oxygen species (ROS) is also involved in the incidence of the degenerative brain diseases. Some evidence support involvement of oxidative stress as an active factor in an Aβ-mediated neuropathy, by triggering or facilitating neurodegeneratio by widespread molecular shapes hindering neuron homeostasis. However, the clinical benefit of the NMDA receptor antagonists and a direct blocker of the neuron channel are debatable because the NMDA receptor antagonists and the direct blocker have the lack of remarkable efficiency or serious side effects.

As normal subjects are getting older, the normal subjects suffer from some degree of memory impairment, but symptoms such as a change in personality which are specifically shown to Alzheimer's patients are not shown, which is called a mild cognitive impairment (MCI). The MCI is considered as a prodrome of Alzheimer's disease, and characterized by a short-term memory loss, a spatial memory loss, and emotional imbalance, and the prodrome is classified into stages. Among the prodromes, the MCI related with the memory loss is called an amnestic MCI, and probability that a 65-year-old normal person is converted to an Alzheimer patient within a certain period is 1 to 3%, whereas in a group with the amnestic MCI, eight out of ten people are converted to Alzheimer patients, and in the case of the amnestic MCI, it is considered that possibility to be developed to Alzheimer's dementia is high.

Parkinson's disease as a chronic progressive, degenerative disease of a nervous system that rest tremor, mortis, bradypragia, and postural instability characterfully appear shows a neuropathologic characteristic in which a nerve cell of dopamine distributed in substantia nigra of a brain (substantia nigra pars compacta, SNc) is gradually lost (Calne et al., 1983, Heikkila 1984). A parkinsonian patient is estimated as approximately 1% of population in approximately 60 ages or more. A cause of the Parkinson's disease is not definitely established, but 'multifactorial hypothesis' that a genetic factor and an environmental factor interact with each other is most commonly accepted. The Parkinson's disease occurs for most of parkinsonian patients without a family history, but approximately 10% appear as a familial Parkinson's disease.

As a symptomatic therapy agent for increasing the reduced amount of dopamine of the Parkinson's disease, L-Dopa is generally used at present. After L-Dopa is used, L-Dopa makes a progress of the Parkinson's disease slow and shows reduction of clinical symptoms, but when L-Dopa is taken for a long time, a side effect such as an involuntary movement, vomiting, or the like is caused (Clarke and Deane, 2001). Besides, medicines used to therapy the Parkinson's disease include Dopamine Agonists, catechol-O-methyltransferase inhibitor (COMT inhibitor), monoamine oxidase B (MAO-B inhibitors), Anti-cholinergics, and the like. An animal model used to research the Parkinson's disease is an animal model using 6-hydroxydopamine (6-OHDA), rotenone, or 1-methyl-4-phenyl-1,2,3,6-tetrahydropyridine (MPTP).

Among them, it was first known that MPTP causes the Parkinson's disease for human by drug addicts in 1982 and this shows the clinical symptoms clinically similar in primates and mouse as well as people, and as a result, the MPTP is evaluated as an appropriate experimental animal model to research a condition physiology change of the Parkinson's disease. Mechanisms of injury of the dopamine nerve cell by the MPTP has not yet definitely appeared, but in recent years, it has been reported that inflammation increases in cerebrums by MPTP exposure and the inflammation is an important process for a physiology research of the Parkinson's disease. Since the MPTP causes acute degeneration of a nigrostriatal pathway in the mouse and monkey, the MPTP has been used as a useful Parkinson model. Further, it has been known that the animal experiment model by the MPTP as an acute inflammation step of the Parkinson's disease is suitable for researching a therapy technology of function damage of mitochondria and cell death by oxidative stress or a neuroprotection effect of drug.

Epilepsy as a chronic disease group due to repeated occurrence of an epilepsy seizure even though there is no cause factor which may cause a single epilepsy seizure, that is, physical abnormality accompanies neurobiological, mental, cognitive, and social changes (Robert et al., 2005). Attack rate and prevalence rate of the epilepsy show a U shape in which the attack rate and the prevalence rate are highest and thereafter, abruptly decrease within 1 year after birth and abruptly increases in an old generation of 60 ages or more, and main causes include stroke, congenital deformity, head injury, encephalitis, a brain tumor, degenerative encephalopathy, inheritance, a premature baby, damage before and after childbirth, and the like.

As a representative animal experiment model used for researching the epilepsy, a white mouse epilepsy model induced by Kainic acid has neuroexcitotoxicity and an epilepsy seizure through a Kainic acid receptor and accompanies cognitive impairment and damage of the nerve cell.

*Houttuynia cordata* (THUNB.) as turning of *Houttuynia cordata* (THUNB.) which is a plant of Saururaceae inhibits in a southeast area of Asia, particularly, Japan, Korea, and the like. The *Houttuynia cordata* is also called ten medicines because of ten medicinal effects and it is derived that a stem is similar as a sweet potato leaf and when a fresh leaf is touched, a smell of fish stunk up to be called *Houttuynia cordata*. *Houttuynia cordata* may be used medicinally or edibly and is classified as animals and plants of which only a minimum amount may be used as supplementary material in food code and food raw material classification and it has been widely known that *Houttuynia cordata* has cardiac, diuretic, antibiotic, detoxification, and anticancer effects pharmacologically, and *Houttuynia cordata* is used as cosmetics and health functional food that assist detoxification and beauty privately.

It is reported that the *Houttuynia cordata* contains a lot of decanoyl acetaldehyde compounds that have antibiotic, antivirus, and fungal inhibition effects and flavonoid-series compounds that show diuretic, cardiac, and evacuation effects. In particular, it is written in a Botanical List that the *Houttuynia cordata* removes a boil, poison, and the like in addition to a fever alleviation action, and it is written in Jungyang dictionary that the *Houttuynia cordata* clean blood, removes inflammation, and helps urine drainage. Meanwhile, *Houttuynia cordata* as a medicinal plant used in herbal and private remedies and in Korean Patent Registration No. 521813 as the related art using the medicinal plant discloses a pharmaceutical composition containing a mixed crude medicine such as a soybean, ganoderma, *Houttuynia cordata*, feeding mugwort, licorice, and the like as an effective component is less and safe in a side effect and toxicity, and is used for anticancer therapy, reinforcement of immunization, and therapy of artery hardening, and a manufacturing method thereof.

*Ampelopsis japonica* Makino as an obese tuberous root of *ampelopsis japonica* has a shape in which both ends are sharpened in a long oval shape or a pyramidal shape. Since the taste is bitter and a property is cold, *ampelopsis japonica* Makino cools heat and release poison. *Ampelopsis japonica* Makino is used for taking medicine or external use, and carbunculosis, and the like, are controlled and new skin is granulated, and when leprosy or abscess is not treated by a blue heat action or new skin is treated by granulating new skin when damage is applied with water or fire.

Accordingly, while the inventors effort the development of a natural substance having treating and prevention effects for dementia, Parkinson's disease, or epilepsy, the inventors confirm that an extract of *Houttuynia cordata* or a mixture of an extract of *Houttuynia cordata* and an extract of *Ampelopsis japonica* Makino has a cognition improved effect in an Amyloid-β (Abeta) oligomer toxicity induced model of a white mouse, a cell protection effect for Amyloid-β induced toxicity in cortical and hippocampal cells, a cell protection effect for a 6-hydroxydopamine (6-OHDA) induced toxicity in an SH-SY5Y cell and a PC12 cell, and a cognition improved effect and a cell protection effect in a Kainic acid toxicity induced model of a white mouse to find that the extract of *Houttuynia cordata* or the mixture of the extract of *Houttuynia cordata* and the extract of *Ampelopsis japonica* Makino may be effectively used for preventing and treating dementia, Parkinson's disease, or epilepsy, thereby completing the present invention.

DISCLOSURE

Technical Problem

The present invention has been made in an effort to provide a pharmaceutical composition of containing an extract of *Houttuynia cordata* (THUNB.) for preventing and treating dementia, Parkinson's disease, or epilepsy, and a composition for health foods for preventing and improving dementia, Parkinson's disease, or epilepsy.

Technical Solution

An exemplary embodiment of the present invention provides a pharmaceutical composition containing an extract of Houttuynia cordata (THUNB.) as an active ingredient for preventing and treating dementia, Parkinson's disease, or epilepsy.

Further, an exemplary embodiment of the present invention provides a pharmaceutical composition containing an extract of Houttuynia cordata as an active ingredient for preventing and treating Parkinson's disease.

Further, an exemplary embodiment of the present invention provides a pharmaceutical composition containing an extract of Houttuynia cordata as an active ingredient for preventing and treating epilepsy.

Further, an exemplary embodiment of the present invention provides a method for preventing dementia, Parkinson's disease, or epilepsy including injecting an extract of Houttuynia cordata into an object.

Further, an exemplary embodiment of the present invention provides a method for treating dementia, Parkinson's disease, or epilepsy including injecting an extract of Houttuynia cordata into an object having dementia, Parkinson's disease, or epilepsy.

Further, an exemplary embodiment of the present invention provides a use of an extract of Houttuynia cordata for use in preparation of a pharmaceutical composition for preventing or improving dementia, Parkinson's disease, or epilepsy.

Further, an exemplary embodiment of the present invention provides a pharmaceutical composition containing a mixture of an extract of Houttuynia cordata and an extract of Ampelopsis japonica Makino as an active ingredient for preventing and treating dementia.

Further, an exemplary embodiment of the present invention provides a pharmaceutical composition containing a mixture of an extract of Houttuynia cordata and an extract of Ampelopsis japonica Makino as an active ingredient for preventing and treating Parkinson's disease.

Further, an exemplary embodiment of the present invention provides a pharmaceutical composition containing a mixture of an extract of Houttuynia cordata and an extract of Ampelopsis japonica Makino as an active ingredient for preventing and treating epilepsy.

Further, an exemplary embodiment of the present invention provides a method for preventing dementia, Parkinson's disease, or epilepsy including injecting a mixture of an extract of Houttuynia cordata and an extract of Ampelopsis japonica Makino into an object.

Further, an exemplary embodiment of the present invention provides a method for treating dementia, Parkinson's disease, or epilepsy including injecting a mixture of an extract of Houttuynia cordata and an extract of Ampelopsis japonica Makino into an object.

Further, an exemplary embodiment of the present invention provides a use of a mixture of an extract of Houttuynia cordata and an extract of Ampelopsis japonica Makino for use in preparation of a pharmaceutical composition for preventing or improving dementia, Parkinson's disease, or epilepsy.

Further, an exemplary embodiment of the present invention provides a composition for health foods containing an extract of Houttuynia cordata as an active ingredient for preventing and improving dementia.

Further, an exemplary embodiment of the present invention provides a composition for health foods containing an extract of Houttuynia cordata as an active ingredient for preventing and improving Parkinson's disease.

Further, an exemplary embodiment of the present invention provides a composition for health foods containing an extract of Houttuynia cordata as an active ingredient for preventing and improving epilepsy.

Further, an exemplary embodiment of the present invention provides a use of an extract of Houttuynia cordata for use in preparation of a composition for health foods for preventing or improving dementia, Parkinson's disease, or epilepsy.

Further, an exemplary embodiment of the present invention provides a composition for health foods containing a mixture of an extract of Houttuynia cordata and an extract of Ampelopsis japonica Makino as an active ingredient for preventing and improving dementia.

Further, an exemplary embodiment of the present invention provides a composition for health foods containing a mixture of an extract of Houttuynia cordata and an extract from Ampelopsis japonica Makino as an active ingredient for preventing and improving Parkinson's disease.

Further, an exemplary embodiment of the present invention provides a composition for health foods containing a mixture of an extract of Houttuynia cordata and an extract of Ampelopsis japonica Makino as an active ingredient for preventing and improving epilepsy.

Further, an exemplary embodiment of the present invention provides a use of a mixture of an extract of Houttuynia cordata and an extract of Ampelopsis japonica Makino for use in preparation of a composition for health foods for preventing or improving dementia, Parkinson's disease, or epilepsy.

Advantageous Effects

According to the exemplary embodiment of the present invention, since it was confirmed that the extract of Houttuynia cordata (THUNB.) of the present invention or the mixture of the extract of Houttuynia cordata and the extract of Ampelopsis japonica Makino had an improved effect of a cognition function in a Amyloid-β (Abeta) oligomer or scopolamine toxicity induced model of a white mouse, had a cell protection effect and a cell death suppression effect in an Amyloid-β induced dementia model, had the cell protection effect in a 6-hydroxydopamine (6-OHDA) induced Parkinson's disease model, and had the cell protection effect in a Kainic acid induced epilepsy model, the extract of Houttuynia cordata or the mixture of the extract of Houttuynia cordata and the extract of Ampelopsis japonica Makino may be effectively used in the development of the pharmaceutical composition for preventing and treating dementia, Parkinson's disease, or epilepsy and the composition for health foods for preventing and treating dementia, Parkinson's disease, or epilepsy.

DESCRIPTION OF DRAWINGS

FIG. 1 is a graph illustrating improvement in a cognition function of an extract of Houttuynia cordata for amyloid-β (Abeta) oligomer toxicity in a white mouse.

HCW: Water extract of Houttuynia cordata

FIG. 2 is a graph illustrating improvement in a cognition function of an extract of Houttuynia cordata for scopolamine toxicity in a white mouse.

HCW: Water extract of Houttuynia cordata

FIG. 3 is a graph illustrating a cell survival rate, after treating an extract of Houttuynia cordata or a mixture of an extract of Houttuynia cordata and an extract of Ampelopsis japonica Makino in a cortical cell.

HCW:AJW: Mixture of water extract of Houttuynia cordata and water extract of Ampelopsis japonica Makino HCE:AJE: Mixture of ethanol extract of *Houttuynia cordata* and ethanol extract of *Ampelopsis japonica* Makino HCW: Water extract of *Houttuynia cordata*; and HCE: Ethanol extract of *Houttuynia cordata*

FIG. 4 is a graph illustrating a cell survival rate of pre-treating an extract of *Houttuynia cordata* or a mixture of an extract of *Houttuynia cordata* and an extract of *Ampelopsis japonica* Makino for amyloid-β (Abeta) toxicity treating in a cortical cell.

HCW:AJW: Mixture of water extract of *Houttuynia cordata* and water extract of *Ampelopsis japonica* Makino HCE:AJE: Mixture of ethanol extract of *Houttuynia cordata* and ethanol extract of *Ampelopsis japonica* Makino HCW: Water extract of *Houttuynia cordata*; and HCE: Ethanol extract of *Houttuynia cordata*

FIG. 5 is a graph illustrating a cell survival rate, after treating an extract of *Houttuynia cordata* or a mixture of an extract of *Houttuynia cordata* and an extract of *Ampelopsis japonica* Makino in a hippocampal cell.

HCW:AJW: Mixture of water extract of *Houttuynia cordata* and water extract of *Ampelopsis japonica* Makino; and HCW: Water extract of *Houttuynia cordata*

FIG. 6 is a graph illustrating a cell survival rate of pre-treating an extract of *Houttuynia cordata* or a mixture of an extract of *Houttuynia cordata* and an extract of *Ampelopsis japonica* Makino for amyloid-β (Abeta) toxicity treating in a hippocampal cell.

HCW:AJW: Mixture of water extract of *Houttuynia cordata* and water extract of *Ampelopsis japonica* Makino; and HCW: Water extract of *Houttuynia cordata*

FIG. 7 is a graph illustrating a cell survival rate, after treating an extract of *Houttuynia cordata* or a mixture of an extract of *Houttuynia cordata* and an extract of *Ampelopsis japonica* Makino in a SH-SY5Y cell.

HCW:AJW: Mixture of water extract of *Houttuynia cordata* and water extract of *Ampelopsis japonica* Makino HCE:AJE: Mixture of ethanol extract of *Houttuynia cordata* and ethanol extract of *Ampelopsis japonica* Makino HCW: Water extract of *Houttuynia cordata*; and HCE: Ethanol extract of *Houttuynia cordata*

FIG. 8 is a graph illustrating a cell survival rate of pre-treating of an extract of *Houttuynia cordata* or a mixture of an extract of *Houttuynia cordata* and an extract of *Ampelopsis japonica* Makino for 6-hydroxydopamine (6-OHDA)-induced toxicity in a SH-SY5Y cell.

HCW:AJW: Mixture of water extract of *Houttuynia cordata* and water extract of *Ampelopsis japonica* Makino HCE:AJE: Mixture of ethanol extract of *Houttuynia cordata* and ethanol extract of *Ampelopsis japonica* Makino HCW: Water extract of *Houttuynia cordata*; and HCE: Ethanol extract of *Houttuynia cordata*

FIG. 9 is a graph illustrating a cell survival rate, after treating a mixture of an extract of *Houttuynia cordata* and an extract of *Ampelopsis japonica* Makino in a PC12 cell.

HCW:AJW: Mixture of water extract of *Houttuynia cordata* and water extract of *Ampelopsis japonica* Makino; and HCE:AJE: Mixture of ethanol extract of *Houttuynia cordata* and ethanol extract of *Ampelopsis japonica* Makino FIG. 10 is a graph illustrating a cell survival rate of pre-treating of a mixture of an extract of *Houttuynia cordata* and an extract of *Ampelopsis japonica* Makino for 6-OHDA-induced toxicity in a PC12 cell.

HCW:AJW: Mixture of water extract of *Houttuynia cordata* and water extract of *Ampelopsis japonica* Makino; and HCE:AJE: Mixture of ethanol extract of *Houttuynia cordata* and ethanol extract of *Ampelopsis japonica* Makino FIG. 11 is a graph illustrating a hippocampal cell protecting effect of an extract of *Houttuynia cordata* for Kainic acid toxicity in a white mouse.

HCW: Water extract of *Houttuynia cordata*

FIG. 12 is a graph illustrating an improved effect in a cognition function of an extract of *Houttuynia cordata* for Kainic acid toxicity in a white mouse.

HCW: Water extract of *Houttuynia cordata*

BEST MODE

Hereinafter, the present invention will be described in detail.

The present invention provides a pharmaceutical composition containing an extract of *Houttuynia cordata* as an active ingredient for preventing and treating dementia.

Further, the present invention provides a pharmaceutical composition containing an extract of *Houttuynia cordata* as an active ingredient for preventing and treating Parkinson's disease.

Further, the present invention provides a pharmaceutical composition containing an extract of *Houttuynia cordata* as an active ingredient for preventing and treating epilepsy.

Further, the present invention provides a method for preventing and treating dementia, Parkinson's disease, or epilepsy including injecting an extract of *Houttuynia cordata* into an object.

Further, the present invention provides a method for treating dementia, Parkinson's disease, or epilepsy including injecting an extract of *Houttuynia cordata* into an object having dementia, Parkinson's disease, or epilepsy.

Further, the present invention provides a use of an extract of *Houttuynia cordata* for use in preparation of a pharmaceutical composition for preventing or improving dementia, Parkinson's disease, or epilepsy.

The *Houttuynia cordata* may be used without limitation such as a grown or commercial thing.

The dementia may be any one selected from a group consisting of Alzheimer's disease, vascular dementia, or mild cognitive impairment (MCI), but is not limited thereto.

The extract of *Houttuynia cordata* may be prepared by the following steps, but is not limited thereto:

1) extracting dried *Houttuynia cordata* by adding an extractant;

2) filtering the extract of the step 1); and 3) press-concentrating the filtered extract of the step 2).

In the method, the extractant of the step 1) may be water, alcohol, or a mixture thereof, preferably, uses a solvent selected from lower alcohol of $C_1$ to $C_2$ or a mixed solvent thereof. It is preferable to use an aqueous solution of 70% ethanol, but is not limited thereto. An amount of the extractant is preferably 5 to 15 times of a dried weight of *Houttuynia cordata*, and more preferably 7 to 10 times, but is not limited thereto. The extraction method may use extraction methods such as hot-water extraction, immersion extraction, reflux extraction, or ultrasonic extraction, but is not limited thereto A temperature during extraction is preferably 10° C. to 100° C., and more preferably a room temperature. The extraction time is preferably 30 minutes to 3 hours, and more preferably 1 to 2 hours, but is not limited thereto. The extraction number is preferably 1 to 5, and more preferably 3, but is not limited thereto.

In the method, the press-concentrating of step 3) may use a decompression concentrator or a vacuum rotary evaporator, but is not limited thereto. Further, the drying may be freeze-drying, but is not limited thereto.

The inventors confirmed that an effect of improving a cognition function was measured in an amyloid-β (Abeta) oligomer induced toxicity model of a white mouse for the extract of *Houttuynia cordata*, and as a result, the cognition function was significantly increased by injecting the extract of *Houttuynia cordata* (see FIG. 1).

Further, the inventors confirmed that an effect of improving a cognition function was measured in a scopolamine induced toxicity model of the white mouse for the extract of *Houttuynia cordata*, and as a result, the cognition function was significantly increased by injecting the extract of *Houttuynia cordata* (see FIG. 2).

Further, the inventors confirmed that in order to confirm a cell protection effect in a cortical cell of the extract of *Houttuynia cordata*, a cell survival rate was measured according to amyloid-β (Abeta) induced toxicity, and as a result, the cell survival rate was significantly increased when treating the extract of *Houttuynia cordata* to have the cell protection effect (see FIGS. 3 and 4).

Further, the inventors confirmed that in order to confirm a cell protection effect in a hippocampal cell of the extract of *Houttuynia cordata*, a cell survival rate was measured according to amyloid-β (Abeta) induced toxicity, and as a result, the cell survival rate was significantly increased when treating the extract of *Houttuynia cordata* to have the cell protection effect (see FIGS. 5 and 6).

Further, the inventors confirmed that in order to confirm a cell protection effect in an SH-SY5Y cell of the extract of *Houttuynia cordata*, a cell survival rate was measured according to amyloid-β (Abeta) induced toxicity, and as a result, the cell survival rate was significantly increased when treating the extract of *Houttuynia cordata* to have the cell protection effect (see FIGS. 7 and 8).

Further, the inventors confirmed that effects of protecting a hippocampal cell and improving a cognition function were measured in a Kainic acid induced toxicity model of the white mouse for the extract of *Houttuynia cordata*, and as a result, the hippocampal cell was significantly increased, and the cognition function was significantly increased by injecting the extract of *Houttuynia cordata* (see FIGS. 11 and 12).

Accordingly, the extract of *Houttuynia cordata* of the present invention has effects of improving the cognition function in the amyloid-β (Abeta) oligomer induced toxicity model of the white mouse and protecting the cell for the amyloid-β and 6-OHDA induced toxicity and has effects of protecting the cell and improving the cognition function in the Kainic acid induced toxicity model, and as a result, may be effectively used as an active ingredient of the pharmaceutical composition for preventing and treating dementia, Parkinson's disease, or epilepsy.

Further, the present invention provides a pharmaceutical composition containing a mixture of an extract of *Houttuynia cordata* and an extract of *Ampelopsis japonica* Makino as an active ingredient for preventing and treating dementia.

Further, the present invention provides a pharmaceutical composition containing a mixture of an extract of *Houttuynia cordata* and an extract of *Ampelopsis japonica* Makino as an active ingredient for preventing and treating Parkinson's disease.

Further, the present invention provides a pharmaceutical composition containing a mixture of an extract of *Houttuynia cordata* and an extract of *Ampelopsis japonica* Makino as an active ingredient for preventing and treating epilepsy.

Further, the present invention provides a method for preventing dementia, Parkinson's disease, or epilepsy including injecting a mixture of an extract of *Houttuynia cordata* and an extract of *Ampelopsis japonica* Makino into an object.

Further, the present invention provides a use of a mixture of an extract of *Houttuynia cordata* and an extract of *Ampelopsis japonica* Makino for use in preparation of a pharmaceutical composition for preventing or improving dementia, Parkinson's disease, or epilepsy.

Further, the present invention provides a method for treating dementia, Parkinson's disease, or epilepsy including injecting a mixture of an extract of *Houttuynia cordata* and an extract of *Ampelopsis japonica* Makino into an object.

The *Houttuynia cordata* or the *Ampelopsis japonica* Makino may be used without limitation such as a grown or commercial product.

The dementia may be any one selected from a group consisting of Alzheimer's disease, vascular dementia, or mild cognitive impairment (MCI), but is not limited thereto.

The mixture of the extract of *Houttuynia cordata* and the extract of *Ampelopsis japonica* Makino may be prepared by the following steps, but is not limited thereto:

1) extracting dried *Houttuynia cordata* or *Ampelopsis japonica* Makino by adding an extractant;

2) filtering the extract of the step 1);

3) press-concentrating the filtered extract of the step 2); and 4) mixing the extract of *Houttuynia cordata* and the extract of *Ampelopsis japonica* Makino obtained in step 3).

In the method, the extractant of step 1) may use water, alcohol, or a mixture thereof, preferably a solvent selected from lower alcohol of C1 to C2 or a mixed solvent thereof, and more preferably, a 70% ethanol aqueous solution, but is not limited thereto. An amount of the extractant is preferably 5 to 15 times of a dried weight of *Houttuynia cordata*, and more preferably 7 to 10 times, but is not limited thereto. The extraction method may use extraction methods such as hot-water extraction, immersion extraction, reflux extraction, or ultrasonic extraction, but is not limited thereto A temperature during extraction is preferably 10° C. to 100° C., and more preferably a room temperature. The extraction time is preferably 30 minutes to 3 hours, and more preferably 1 to 2 hours, but is not limited thereto. The extraction number is preferably 1 to 5, and more preferably 3, but is not limited thereto.

In the method, a mixed ratio of step 4) is preferably 1:1 to 10:1 of the extract of *Houttuynia cordata* and the extract of *Ampelopsis japonica* Makino, and more preferably 1:1 to 10:1, but is not limited thereto.

The inventors confirmed that in order to confirm an cell protection effect in a cortical cell of the mixture of the extract of *Houttuynia cordata* and the extract from *Ampelopsis japonica* Makino, a cell survival rate was measured according to amyloid-β induced toxicity, and as a result, the cell survival rate was significantly increased when treating the mixture of the extract of *Houttuynia cordata* and the extract of *Ampelopsis japonica* Makino to have the cell protection effect (see FIGS. 3 and 4).

Further, the inventors confirmed that in order to confirm an cell protection effect in a hippocampal cell of the mixture of the extract of *Houttuynia cordata* and the extract of *Ampelopsis japonica* Makino, a cell survival rate was measured according to amyloid-β induced toxicity, and as a result, the cell survival rate was significantly increased when treating the mixture of the extract of *Houttuynia cordata* and the extract of *Ampelopsis japonica* Makino to have the cell protection effect (see FIGS. 5 and 6).

Further, the inventors confirmed that in order to confirm an cell protection effect in an SH-SY5Y cell of the mixture of the extract of *Houttuynia cordata* and the extract of *Ampelopsis japonica* Makino, a cell survival rate was measured according to 6-hydroxydopamine (6-OHDA) induced toxicity, and as a result, the cell survival rate was significantly increased when treating the extract of *Houttuynia cordata* to have the cell protection effect (see FIGS. 7 and 8).

Accordingly the mixture of the extract of *Houttuynia cordata* and the extract of *Ampelopsis japonica* Makino of the present invention has the effect for protecting the cell for the amyloid-β and 6-OHDA induced toxicity to be effectively used as an active ingredient of the composition for preventing and treating dementia, Parkinson's disease, or epilepsy.

The composition of the present invention may include 0.1 to 90 wt % of the extract of *Houttuynia cordata* or the mixture of the extract of *Houttuynia cordata* and the extract of *Ampelopsis japonica* Makino with respect to a total weight of the composition, but is not limited thereto.

The composition of the present invention may further include carriers, excipients, and diluents which are generally used in preparation of the pharmaceutical composition.

The composition of the present invention may be orally or parenterally injected, and during the parenteral injection, a method of skin external use, intraperitoneal injection, rectal injection, hypodermic injection, intravenous injection, intramuscular injection, or intrachestal injection may be selected, but is not limited thereto.

The composition of the present invention may be used by oral formulations such as powders, granules, tablets, capsules, suspensions, emulsions, syrups, and aerosols, and formations such as external formulations, suppositories, and sterilized injection solutions according to respective general methods. The carriers, the excipients, and the diluents which may be included in the composition may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. The formulation is prepared by using diluents such as fillers, extenders, binders, wetting agents, disintegrating agents and surfactants, or excipients which are generally used. A solid formulation for oral injection includes tablets, pills, powders, granules, capsules, and the like, and the solid formulation is prepared by mixing at least one of excipients, for example, starch, calcium carbonate, sucrose or lactose, gellatine, and the like with the extract from *Houttuynia cordata* or the mixture of the extract from *Houttuynia cordata* and the extract of *Ampelopsis japonica* Makino. Further, lubricants such as magnesium stearate, and talc are used in addition to simple excipients. A liquid formulation for oral injection may include suspension, solutions, emulsions, syrups, or the like, and may include various excipients, for example, wetting agents, sweeteners, aromatics, preservatives, or the like in addition to water and liquid paraffin which are commonly used simple dilutes. The formulation for parenteral injection includes sterilized aqueous solutions, non-aqueous solvents, suspensions, emulsions, lyophilized formulations, and suppositories. As the non-aqueous solvent and the suspensions, vegetable oil such as propylene glycol, polyethylene glycol, and olive oil, and injectable ester such as ethyl oleate may be used. As a base compound of the suppositories, witepsol, macrogol, tween 61, cacao butter, laurinum, glycerogelatin, or the like, may be used.

A preferable injection amount of the composition of the present invention varies according to patient's condition and body weight, disease severity, drug forms, injection route and period, but may be properly selected by those skilled in the art. However, for the preferable effect, the composition may be injected by 0.0001 to 1 g/kg per one day, and preferably 0.001 to 200 mg/kg, but is not limited thereto. The injection may be once a day, and several times a day. The injection amount does not limit the scope of the present invention in any way.

Further, the present invention provides a composition for health foods containing an extract of *Houttuynia cordata* as an active ingredient for preventing and improving dementia.

Further, the present invention provides a composition for health foods containing an extract of *Houttuynia cordata* as an active ingredient for preventing and improving Parkinson's disease.

Further, the present invention provides a composition for health foods containing an extract of *Houttuynia cordata* as an active ingredient for preventing and improving epilepsy.

Further, the present invention provides a use of an extract of *Houttuynia cordata* for use in preparation of a composition for health foods for preventing or improving dementia, Parkinson's disease, or epilepsy.

The dementia may be any one selected from a group consisting of Alzheimer's disease, vascular dementia, or mild cognitive impairment (MCI), but is not limited thereto.

The extract of *Houttuynia cordata* of the present invention has the effect of improving the cell for the amyloid-β and 6-OHDA induced toxicity and has the cell protection effect and the cognition function improving effect in the scopolamine, amyloid-β, and Kainic acid induced models, and as a result, may be effectively used as an active ingredient of the health foods for preventing and improving dementia, Parkinson's disease, or epilepsy.

Further, the present invention provides a composition for health foods containing a mixture of an extract of *Houttuynia cordata* and an extract of *Ampelopsis japonica* Makino as an active ingredient for preventing and improving dementia.

Further, the present invention provides a composition for health foods containing a mixture of an extract of *Houttuynia cordata* and an extract of *Ampelopsis japonica* Makino as an active ingredient for preventing and improving Parkinson's disease.

Further, the present invention provides a composition for health foods containing a mixture of an extract of *Houttuynia cordata* and an extract of *Ampelopsis japonica* Makino as an active ingredient for preventing and improving epilepsy.

Further, the present invention provides a use of a mixture of an extract of *Houttuynia cordata* and an extract of *Ampelopsis japonica* Makino for use in preparation of a composition for health foods for preventing or improving dementia, Parkinson's disease, or epilepsy.

The dementia may be any one selected from a group consisting of Alzheimer's disease, vascular dementia, or mild cognitive impairment (MCI), but is not limited thereto.

The mixture of the extract of *Houttuynia cordata* and the extract of *Ampelopsis japonica* Makino of the present invention has the effect for protecting the cell for the amyloid-β and 6-OHDA induced toxicity to be effectively used as an active ingredient of the health foods for preventing and improving dementia, Parkinson's disease, or epilepsy.

Kinds of foods are not particularly limited. Examples of the foods are drinks, meat, sausages, bread, biscuits, rice cake, chocolates, candies, snacks, cookies, pizza, noodles, and other noodles, gums, dairy products including ice cream, various soups, beverages, alcoholic drinks, vitamin complexes, and the like, and include all health foods in general meaning.

The extract of *Houttuynia cordata* or the mixture of the extract of *Houttuynia cordata* and the extract of *Ampelopsis japonica* Makino of the present invention may be added into the foods or used together with other foods or other food ingredients, and may be properly used according to a general method. A mixed amount of the active ingredient may be properly determined according to a use purpose (prevention or improvement) thereof. Generally, the amount of the extract in the health foods may be added with 0.01 to 15 wt % with respect to a total food weight, and the composition of the health drink may be added with a ratio of 0.02 to 5 g, preferably 0.3 to 1 g based on 100 ml. However, in the case of long-term ingestion for the purpose of health and hygiene or health control, the amount may be the range or less, and the active ingredient may be used with the amount of the range or more because there is no problem in terms of safety.

The composition of the health functional beverage of the present invention is not particularly limited to other ingredients except for containing the extract of *Houttuynia cordata* or the mixture of the extract of *Houttuynia cordata* and the extract of *Ampelopsis japonica* Makino as an essential ingredient with the described ratio, and may contain various flavoring agents or natural carbohydrates as an additional ingredient like a general beverage. Examples of the aforementioned natural carbohydrates include general sugars, such as monosaccharides, that is, glucose, fructose, and the like; disaccharides, for example, maltose, sucrose, and the like; and polysaccharides, for example, dextrin, cyclodextrin, and sugar alcohols, such as xylitol, sorbitol, and erythritol. As flavoring agents other than the aforementioned flavoring agents, natural flavoring agents (thaumatin, stevia extract (for example, rebaudioside A, glycyrrhizin, and the like.), and synthetic flavoring agents (saccharin, aspartame, and the like.) may be advantageously used.

The foods of the present invention may contain various nutrients, vitamins, minerals (electrolytes), flavoring agents such as synthetic flavoring agents and natural flavoring agents, colorants, and enhancers (cheese, chocolate, and the like.), pectic acid and salts thereof, alginic acid and salts thereof, organic acid, protective colloidal thickening agents, pH adjusting agents, stabilizers, preservatives, glycerin, alcohol, carbonated agents used in carbonated drinks, and the like, in addition to the ingredients. In addition, the extract of the present invention may contain pulps for preparing natural fruit juices, fruit juice beverages, and vegetable beverages. The ingredients may be used alone or in combination thereof. The ratio of the additives is not important, but is generally selected from a range of 0 to about 20 parts by weight with respect to 100 parts by weight of the extract of the present invention.

Hereinafter, the present invention will be described in detail by Examples, Experimental Examples, and Preparation Examples.

However, the following Examples, Experimental Examples, and Preparation Examples just exemplify the present invention, and the contents of the present invention are not limited to the following Examples, Experimental Examples, and Preparation Examples.

EXAMPLE 1

Preparation of Extracts of *Houttuynia cordata* (THUNB.) and *Ampelopsis japonica* Makino <1-1> Preparation of Water Extract of *Houttuynia cordata*

100 g of *Houttuynia cordata* buying in JungDo pharmaceutical corporation (Seoul) was finely crushed, reflux-extracted for 2 hours at 100° C. by setting distilled water to an amount of 10 times of *Houttuynia cordata*, and then vacuum-filtrated by using a Whatman filter paper #2. The filtrate was dry-powdered, stored at −20° C., and used to be prepared during the experiment, and yield was 16.1%.

<1-2> Preparation of Ethanol Extract of *Houttuynia cordata*

100 g of *Houttuynia cordata* buying in JungDo pharmaceutical corporation (Seoul) was added in 1,000 mL of 70% ethanol and extracted while stirred for 24 hours, and then filtrated by using a Whatman filter paper #2. A sample obtained by vacuum-concentrating (Rotavapor R-200, heating bath B-490, BUCHI; Flawil, Swizerland) the filtrate at 50° C. was freeze-dried and stored at −20° C., and used to be prepared during the experiment, and yield was 8.20%.

<1-3> Preparation of Water Extract of *Ampelopsis japonica* Makino

The water extract of *Ampelopsis japonica* Makino was prepared by the same method as Example <1-1>.

<1-4> Preparation of Ethanol Extract of *Ampelopsis japonica* Makino

The ethanol extract of *Ampelopsis japonica* Makino was prepared by the same method as Example <1-2>.

<1-5> Preparation of Mixture of Extract of *Houttuynia cordata* and Extract of *Ampelopsis japonica* Makino The mixture of the extract of *Houttuynia cordata* and the extract of *Ampelopsis japonica* Makino was prepared by mixing the extract of *Houttuynia cordata* and the extract of *Ampelopsis japonica* Makino which are prepared in Examples <1-1> to <1-4> above with a ratio of 1:1 or 10:1.

EXPERIMENTAL EXAMPLE 1

Confirm of Anti-Dementia Effect of Extract of *Houttuynia Cordata* In Vivo

<1-1> Preparation of Experimental Animal

As an experimental animal, a male ICR mouse (8-week old, 30 to 32 g, Korea bio) was adopted, and adapted for 7 days in an animal chamber by controlling a temperature of 23±1° C., humidity of 60±10%, and day and night for every 12 hours and sufficiently supplying water and a general diet, and then used in the experiment. 50, 100, or 200 mg/kg of the extract of *Houttuynia cordata* was orally injected once a day for 10 days, and at the fourth day after the drug injection, amyloid-β oligomer was directly injected in a hippocampus of the brain with 10 μm, and as a result, a dementia analog model was induced.

<1-2> Behavioral Test

In order to evaluate an effect of the extract of *Houttuynia cordata* for cognition impairment induced by amyloid-β oligomer, a novel object cognition test was performed at fifth day and sixth day after injecting the amyloid-β oligomer. In detail, at the first day of the test, two same objects were put in a box of a width of 45 cm, a length of 45 cm, and a height of 50 cm, the mouse was put in the box and recognized the two objects, and at the second day, one of the two objects in the same box was changed to an object having a different shape, and then a searching time of the mouse for the new object was measured.

As a result, as illustrated in FIG. 1, it was confirmed that a group treated with the extract of *Houttuynia cordata* had an improved cognition function in comparison with a cognition impairment induced by the amyloid-β oligomer (see FIG. 1).

<1-3> Preparation of Experimental Animal

As an experimental animal, a male ICR mouse (6-week old, 30 g, Korea bio) was adopted, and adapted for 7 days in an animal chamber by controlling a temperature of 23±1° C., humidity of 60±10%, and day and night for every 12 hours and sufficiently supplying water and a general diet, and then used in the experiment. 100 mg/kg of the extract of *Houttuynia cordata* was orally injected once, and directly injected into a peritoneal cavity with 1 mg/kg of scopolamine, and as a result, a dementia analog model was induced.

<1-4> Behavioral Test

In order to evaluate an effect of the extract of *Houttuynia cordata* for the cognition impairment induced by scopolamine, a Y-maze test was performed for 30 minutes after injecting the scopolamine. In detail, after the experimental animal was input to a Y path, the path on which the experimental animal moved was recorded, and thus a movement ratio of each different path to a total movement path was calculated.

As a result, as illustrated in FIG. 2, it was confirmed that a group treated with the extract of *Houttuynia cordata* had an improved cognition function in comparison with a cognition impairment induced by the scopolamine (see FIG. 2).

EXPERIMENTAL EXAMPLE 2

Confirm of Anti-Dementia Effect of Extract of *Houttuynia Cordata* In Vivo

<2-1> Confirm of Cell Protection Effect in Cortical

An amyloid plaque generated by accumulating Amyloid-β (Abeta) was accumulated in the brain and known as a substance that killed brain cells, and was a substance used for a dementia research. Toxicity for a cortical cell was caused by using a substance artificially aggregating Abeta (25-35), and as a result, the cell protection effect of the extract of *Houttuynia cordata* or the mixture of the extract of *Houttuynia cordata* and the extract of *Ampelopsis japonica* Makino was measured by using an MTT assay. In detail, first, only a cortical portion was separated from a 18-day fetal of Sprague-Dawley rats (Korea bio, Seoul), mechanically decomposed to obtain cells, and the cells were inoculated in a 96 well plate pre-coated with poly-L-lysine with $1.5 \times 10^4$/well, and then cultured for 7 days. Thereafter, the cells were cultured in a B27 free neurobasal media for 24 hours by treating or non-treating 8 μg of Amyloid-β (Abeta) after 30 minutes of treatment of the extract of *Houttuynia cordata* of Example 1 or the mixture of the extract of *Houttuynia cordata* and the extract of *Ampelopsis japonica* Makino for each concentration, and after 3 hours of 1 mg/mL MTT treatment, formazan was dissolved with DMSO, and then absorbance was measured in 570 nm.

As a result, as illustrated in FIGS. 3 and 4, when the extract of *Houttuynia cordata* or the mixture of the extract of *Houttuynia cordata* and the extract of *Ampelopsis japonica* Makino was treated alone in the cortical cell, it was confirmed that a cell survival rate was not influenced. Further, in the case of the Abeta toxicity treatment, the cell survival rate was reduced as compared with a control group, and in a pre-treatment group of the extract of *Houttuynia cordata* or the mixture of the extract of *Houttuynia cordata* and the extract of *Ampelopsis japonica* Makino, it was confirmed that a significant cell protection effect was illustrated (see FIGS. 3 and 4).

<2-2> Cell Protection Effect in Hippocampal

In order to confirm the cell protection effect of the extract of *Houttuynia cordata* or the mixture of the extract of *Houttuynia cordata* and the extract of *Ampelopsis japonica* Makino, only a hippocampal portion was separated from a 18-day fetal of Sprague-Dawley rats (Korea bio, Seoul), mechanically decomposed to obtain cells, and the cells were inoculated in a 96 well plate pre-coated with poly-L-lysine with $1.5 \times 10^4$/well, and then cultured for 7 days. Thereafter, the cells were cultured in a B27 free neurobasal media for 24 hours by treating or non-treating 8 μg of Amyloid-β (Abeta) after 30 minutes of treatment of the extract of *Houttuynia cordata* of Example 1 or the mixture of the extract of *Houttuynia cordata* and the extract of *Ampelopsis japonica* Makino for each concentration, and after 3 hours of 1 mg/mL MTT treatment, formazan was dissolved with DMSO, and then absorbance was measured in 570 nm.

As a result, as illustrated in FIGS. 5 and 6, when the extract of *Houttuynia cordata* or the mixture of the extract of *Houttuynia cordata* and the extract of *Ampelopsis japonica* Makino was treated alone in the hippocampal cell, it was confirmed that a cell survival rate was not influenced. Further, in the case of the Abeta toxicity treatment, the cell survival rate was reduced as compared with a control group, and in a pre-treatment group of the extract of *Houttuynia cordata* or the mixture of the extract of *Houttuynia cordata* and the extract of *Ampelopsis japonica* Makino, it was confirmed that a significant cell protection effect was illustrated (see FIGS. 5 and 6).

EXPERIMENTAL EXAMPLE 3

Confirm of Anti-Parkinson's Disease Effect of Extract of *Houttuynia Cordata* In Vivo <3-1> Cell Protection Effect of Extract of *Houttuynia cordata* in SH-SY5Y Cell In order to confirm the cell survival rate of the extract of *Houttuynia cordata* or the mixture of the extract of *Houttuynia cordata* and the extract of *Ampelopsis japonica* Makino for 6-hydroxydopamine (6-OHDA) induced toxicity causing dopamine nervous lesions at an injected portion, fiber neuroblastoma SH-SY5Y cells secreting dopamine cells were inoculated in a 96 well plate pre-coated with Poly-L-lysine with $2 \times 10^4$/well, and then cultured for 2 days, and cultured by treating or non-treating the 6-OHDA, after pre-treating the extract of *Houttuynia cordata* or the mixture of the extract of *Houttuynia cordata* and the extract of *Ampelopsis japonica* Makino dissolved in an FBS free DMEM media for each concentration. The reacted cells were treated at a concentration of MTT 1 mg/mL for 3 hours, and then formazan was dissolved with DMSO, and then absorbance was measured in 570 nm.

As a result, as illustrated in FIGS. 7 and 8, when the extract of *Houttuynia cordata* or the mixture of the extract of *Houttuynia cordata* and the extract of *Ampelopsis japonica* Makino was treated alone in the SH-SY5Y cell, it was confirmed that the cell survival rate was not influenced, and the pre-treatment of the extract of *Houttuynia cordata* or the mixture of the extract of *Houttuynia cordata* and the extract of *Ampelopsis japonica* Makino had a significant cell protection effect with respect to the 6-OHDA toxicity (see FIGS. 7 and 8).

<3-2> Cell Protection Effect of Extract of *Houttuynia cordata* in PC12 Cell

In order to confirm the cell survival rate of the extract of *Houttuynia cordata* or the mixture of the extract of *Houttuynia cordata* and the extract of *Ampelopsis japonica* Makino for 6-OHDA induced toxicity causing dopamine nervous lesions at an injected portion, PC12 cells having a similar differentiation to nervous cells were inoculated in a 96 well with $1.5 \times 10^4$/well, and then cultured for 2 days, and cultured for 4 hours by treating or non-treating 50 μm of the 6-OHDA, after 1 hour of the treatment of the extract of *Houttuynia cordata* or the mixture of the extract of *Hout-* tuynia cordata and the extract of *Ampelopsis japonica* Makino diluted in an FBS free RPMI media for each concentration. The reacted cells were treated at a concentration of MTT 1 mg/mL for 3 hours, and then formazan was dissolved with DMSO, and then absorbance was measured in 570 nm.

As a result, as illustrated in FIGS. 9 and 10, when the extract of *Houttuynia cordata* or the mixture of the extract of *Houttuynia cordata* and the extract of *Ampelopsis japonica* Makino was treated alone in the PC 12 cell, it was confirmed that the cell survival rate was not influenced, and the pre-treatment of the extract of *Houttuynia cordata* or the mixture of the extract of *Houttuynia cordata* and the extract of *Ampelopsis japonica* Makino had a significant cell protection effect with respect to the 6-OHDA toxicity (see FIGS. 9 and 10).

EXPERIMENTAL EXAMPLE 4

Confirm of Anti-Epilepsy Effect of Extract of *Houttuynia cordata* In Vivo

<4-1> Preparation of Experimental Animal

As an experimental animal, a male ICR mouse (10-week old, 34 to 36 g, Korea bio) was adopted, and adapted for 7 days in an animal chamber by controlling a temperature of 23±1° C., humidity of 60±10%, and day and night for every 12 hours and sufficiently supplying water and a general diet, and then used in the experiment. 200 mg/kg of the extract of *Houttuynia cordata* was orally injected once a day for 3 days, and at the third day after the drug injection, 0.4 µg of Kainic acid was directly injected in the lateral ventricle of the brain, and as a result, an epilepsy analog model was induced.

<4-2> Behavioral Test

In order to evaluate an effect of the extract of *Houttuynia cordata* for cognition impairment induced by Kainic acid, a novel object cognition test was performed at the fourth day after injecting the Kainic acid. In detail, at the first day of the test, two same objects were put in a box of a width of 45 cm, a length of 45 cm, and a height of 50 cm, the mouse was put in the box and recognized the two objects, and at the second day, one of the two objects in the same box was changed to an object having a different shape, and then a searching time of the mouse for the new object was measured.

As a result, as illustrated in FIG. 12, it was confirmed that a group treated with the extract of *Houttuynia cordata* had an improved cognition function in comparison with a cognition impairment induced by Kainic acid (see FIG. 12).

<4-3> Confirm of Hippocampal Cell Protection Effect of Extract of *Houttuynia cordata*

In order to confirm a protection effect for the damage of the hippocampal cell induced by Kainic acid of the extract of *Houttuynia cordata*, Nissl staining was performed. In detail, after the behavior test of the Experimental Example <4-2>, a tissue was extracted, and then a mouse of each group was anesthetized, and a brain tissue was fixed with perfusion and 4% PFA. The brain tissue through the post-fixing process was cut with a thickness of 30 µm by using a freeze slicer, and the tissue of the hippocampal portion was Nissl-strained, and then the protection effect of the extract of *Houttuynia cordata* was analyzed.

As a result, as illustrated in FIG. 11, it was confirmed that the pre-treatment of 200 mg/kg of the extract of *Houttuynia cordata* with respect to the damage to the hippocampal cell induced by Kainic acid suppressed the loss of the hippocampal cell to have the cell protection effect (see FIG. 11).

PREPARATION EXAMPLE 1

Preparation Of Pharmaceutical Formulations

<1-1> Preparation of Powder
Extract of *Houttuynia cordata* of Example <1-1> 2 g
Lactose 1 g
The ingredients were mixed and filled in an airtight bag to prepare a powder.

<1-2> Preparation of Tablet
Extract of *Houttuynia cordata* of Example <1-1> 100 mg
Corn starch 100 mg
Lactose 100 mg
Magnesium stearate 2 mg
The ingredients were mixed, and then compressed according to a general method of preparing a tablet to prepare the tablet.

<1-3> Preparation of Capsule
Extract of *Houttuynia cordata* of Example <1-5> 100 mg
Corn starch 100 mg
Lactose 100 mg
Magnesium stearate 2 mg
The ingredients were mixed, and then filled in a gelatin capsule according to a general method of preparing a capsule to prepare the capsule.

<1-4> Preparation of Pill
Extract of *Houttuynia cordata* of Example <1-5> 1 g
Lactose 1.5 g
Glycerin 1 g
Xylitol 0.5 g
The ingredients were mixed, and then prepared so as to be 4 g per 1 pill according to a general method.

<1-5> Preparation of Granule
Extract of *Houttuynia cordata* of Example <1-1> 150 mg
Soybean extract 50 mg
Glucose 200 mg
Starch 600 mg
The ingredients were mixed, and then added with 100 mg of 30% ethanol, and dried at 60° C. to form a granule, and the granule was filled in a bag.

PREPARATION EXAMPLE 2

Preparation of Foods

Foods including the extract of *Houttuynia cordata* of the present invention were prepared as follows.

<2-1> Preparation of Flour Food
0.5 to 5.0 parts of weight of the extract of *Houttuynia cordata* of Example <1-2> was added to flour to prepare bread, cakes, cookies, crackers, and noodles by using the mixture.

<2-2> Preparation of Soups and Gravies
0.1 to 5.0 parts by weight of the extract of *Houttuynia cordata* of Example <1-2> was added into soups and gravies to prepare soups and gravies of meat products, and noodles for health promotion.

<2-3> Preparation of Ground Beef
10 parts by weight of the extract of *Houttuynia cordata* of Example <1-1> was added in ground beef to prepare ground beef for health promotion.

<2-4> Preparation of Dairy Products
5 to 10 parts of weight of the extract of *Houttuynia cordata* of Example <1-1> was added into milk to prepare various dairy products such as butter and ice cream by using the milk.

<2-5> Preparation of Sunsik

Brown rice, barley, glutinous rice, and adlay were pregelatinized by a known method and dried, and pulverized, and then prepared with powder having a grain size of 60 meshes by using a grinder.

Black bean, black sesame, and perilla were also pregelatinized by a known method and dried, and pulverized, and then prepared with powder having a grain size of 60 meshes by using a grinder.

A dry matter obtained by vacuum-concentrating the extract of *Houttuynia cordata* of Example <1-1> in a vacuum concentrator and drying by a spraying and hot wind drier was grinded with a granule size of 60 meshes by using a grinder to obtain a dried powder.

Grains, seeds, and the extract of *Houttuynia cordata* of Example <1-1> which were prepared above were mixed at the following ratio to be prepared.

Grains (30 parts by weight of brown rice, 15 parts of weight of adlay, and 20 parts by weight of barley), Seeds (7 parts by weight of perilla, 8 parts by weight of black bean, and 7 parts by weight of black sesame), Extract of *Houttuynia cordata* of Example <1-1> (3 parts by weight), Ganoderma (0.5 part by weight), and Rehmaina (0.5 part by weight)<

PREPARATION EXAMPLE 3

Preparation of Beverage

<3-1> Preparation of Health Beverage

Sub materials such as Liquid fructose (0.5%), oligosaccharide (2%), sugar (2%), salt (0.5%), and water (75%) and 5 g of the extract of *Houttuynia cordata* in Example <1-2> were homogeneously blended and sterilized at a short time, and then packed in a small packaging container such as a glass bottle and a plastic bottle to prepare the health beverage.

<3-2> Preparation of Vegetable Juices 5 g of the extract of *Houttuynia cordata* in Example <1-1> was added into 1,000 ml of tomato or carrot juice to prepare the vegetable juices.

<3-3> Preparation of Fruit Juices 1 g of the extract of *Houttuynia cordata* in Example <1-1> was added into 1,000 ml of apple or grape juice to prepare the fruit juices.

INDUSTRIAL APPLICABILITY

Since it was confirmed that the extract of *Houttuynia cordata* (THUNB.) of the present invention or the mixture of the extract of *Houttuynia cordata* and the extract of *Ampelopsis japonica* Makino had an improved effect of a cognition function in a Amyloid-β (Abeta) oligomer or scopolamine toxicity induced model of a white mouse, had a cell protection effect and a cell death suppression effect in an Amyloid-β induced dementia model, had the cell protection effect in a 6-hydroxydopamine (6-OHDA) induced Parkinson's disease model, and had the cell protection effect in a Kainic acid induced epilepsy model, the extract of *Houttuynia cordata* or the mixture of the extract of *Houttuynia cordata* and the extract of *Ampelopsis japonica* Makino may be effectively used in the development of the pharmaceutical composition for preventing and treating dementia, Parkinson's disease, or epilepsy and the composition for health foods for preventing and treating dementia, Parkinson's disease, or epilepsy.

What is claimed is:

1. A method for treating Parkinson's disease or epilepsy comprising injecting an effective amount of an extract of *Houttuynia cordata* into a subject having Parkinson's disease or epilepsy.

2. A method for treating dementia, Parkinson's disease, or epilepsy comprising injecting effective amounts of an extract of *Houttuynia cordata* and an extract of *Ampelopsis japonica* into a subject having dementia, Parkinson's disease, or epilepsy.

3. The method of claim 1, wherein the extract is extracted by water, a lower alcohol of $C_1$ to $C_2$, or a mixture thereof.

4. The method of claim 3, wherein the lower alcohol is ethanol or methanol.

5. The method of claim 2, wherein the extract is extracted by water, a lower alcohol of $C_1$ to $C_2$, or a mixture thereof.

6. The method of claim 5, wherein the lower alcohol is ethanol or methanol.

7. The method of claim 2, wherein the mixture of the extract of *Houttuynia cordata* and the extract of *Ampelopsis japonica* Makino has a mixed ratio of 1:1 to 10:1.

8. The method of claim 2, wherein the dementia is any one selected from the group consisting of Alzheimer's disease, vascular dementia, and mild cognitive impairment (MCI).

9. The method of claim 1, wherein the subject has Parkinson's disease.

10. The method of claim 1, wherein the subject has epilepsy.

11. The method of claim 2, wherein the subject has Parkinson's disease.

12. The method of claim 2, wherein the subject has epilepsy.

13. The method of claim 2, wherein the subject has dementia.

14. The method of claim 13 wherein the dementia is any one selected from the group consisting of Alzheimer's disease, vascular dementia, and mild cognitive impairment (MCI).

* * * * *